United States Patent
Holmgren et al.

(10) Patent No.: US 6,565,753 B1
(45) Date of Patent: May 20, 2003

(54) METHOD FOR PURIFICATION OF DEICING FLUID FOR RECOVERY OF GLYCOL

(75) Inventors: Allan Holmgren, Luleå (SE); Peter Mattsson, Luleå (SE)

(73) Assignee: De-Icing, Inc., Stockholm (SE)

( * ) Notice: Subject to any disclaimer, the term of this patent is extended or adjusted under 35 U.S.C. 154(b) by 0 days.

(21) Appl. No.: 09/508,016

(22) PCT Filed: Sep. 18, 1998

(86) PCT No.: PCT/SE98/01685
§ 371 (c)(1),
(2), (4) Date: Jun. 27, 2000

(87) PCT Pub. No.: WO99/15486
PCT Pub. Date: Apr. 1, 1999

(30) Foreign Application Priority Data

Sep. 19, 1997 (SE) ................................................ 9703397

(51) Int. Cl.[7] .............................................. B01D 21/01
(52) U.S. Cl. ................. 210/664; 203/12; 210/667; 210/669; 210/688; 210/724; 568/868; 568/872
(58) Field of Search .................. 568/872, 868, 568/870; 210/664–669, 688, 724–728, 799, 806, 912; 422/120, 122; 203/18, 12, DIG. 16; 244/134 R

(56) References Cited

U.S. PATENT DOCUMENTS

| | | | | |
|---|---|---|---|---|
| 5,411,668 A | * | 5/1995 | Pollmann et al. | 210/259 |
| 5,510,036 A | | 4/1996 | Woyciesjes et al. | 210/664 |
| 5,651,895 A | * | 7/1997 | Gordon | 210/709 |
| 5,904,321 A | * | 5/1999 | Cox et al. | 203/18 |

FOREIGN PATENT DOCUMENTS

CA 2116827 5/1995

OTHER PUBLICATIONS

International–Type Search Report for application No. 9703397–1, dated Apr. 3, 1998.

* cited by examiner

Primary Examiner—Peter A. Hruskoci
(74) Attorney, Agent, or Firm—Merchant & Gould P.C.

(57) ABSTRACT

In the purification of deicing fluid for recovery of glycol, initially solid particles are separated, then dissolved organic compounds and positive and negative ions are separated by an ion exchange in an ion exchanger, and finally water is separated by distillation.

6 Claims, 1 Drawing Sheet

METHOD FOR PURIFICATION OF DEICING FLUID FOR RECOVERY OF GLYCOL

TECHNICAL FIELD

Figure 1:
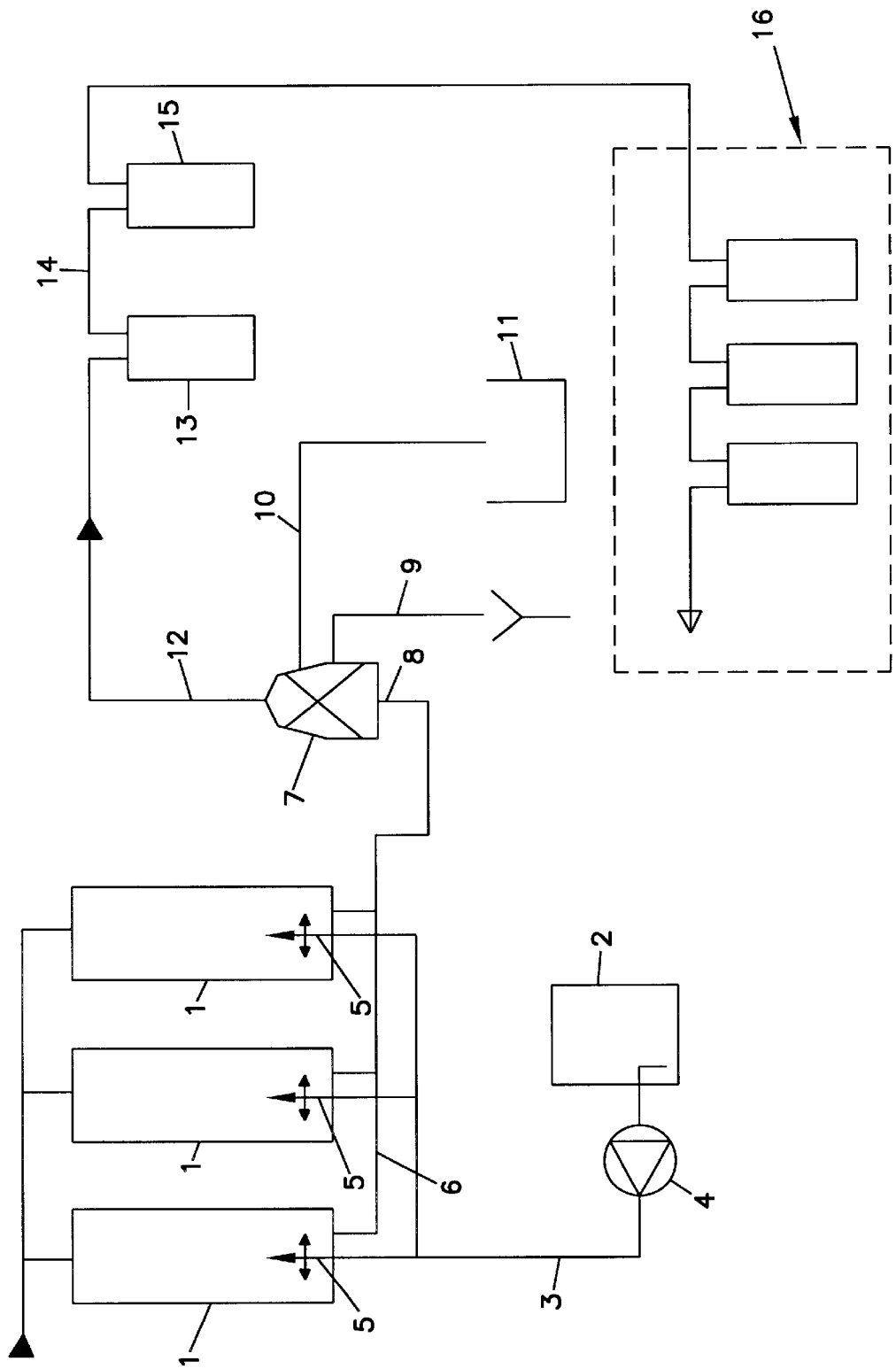

The invention relates to a method and a device for purification of deicing fluid for recovery of glycol, especially purification of deicing fluids from airports, wherein initially solid particles are separated, then dissolved organic compounds and positive and negative ions are separated by ion exchange in an ion exchanger, and finally water is separated by distillation.

STATE OF THE ART

Accumulation of ice on aircraft wings is a well known problem involving great risks in that the surface of the foil changes and in that the weight of the aircraft increases. At present, ice is removed from the wings of the aircraft by spraying them with so called deicing fluid, usually consisting of ethylene glycol, propylene glycol or a mixture thereof and additives of different kinds.

For economical reasons and in order to minimize the environmental impact, it is desirable to recover the deicing fluid to the greatest extent possible. At present, processes exist to purify and concentrate the most common deicing fluid which normally consists of pure glycol (monopropylene, monoethylene or diethylene) having additives of anionic and/or non-ionic tensides, corrosion inhibitors and, in certain cases, colourings and water.

Further development of deicing fluids has, however, resulted in the development of new types having the above mentioned deicing fluid as a basis with the addition of a thickener, the purpose of which is to accomplish a better protection against renewed freezing of the deicing fluid due to fact that the thickener obtains a higher viscosity and therefore remains for a longer time period on an aircraft. This is of great importance on airports having very frequent traffic. The aircraft may then have to wait for long periods of time before takeoff, and it is then of utmost importance that the deicing fluid remains. When the aircraft takes off, the deicing fluid is sheared off.

For the time being, commercial recovery processes comprise filtration, deionization and distillation. The used deicing fluid is collected in the deicing plant and when it enters the recovery plant it normally has a glycol content of about 15–25% by weight in a mixture with water, solid particles, salts, etc. The initial filtration is, for instance, presently accomplished in a cotton filter having a mesh width of down to about 5–10 $\mu$m. After filtration, the deicing fluid is passed through ion exchange filters to separate dissolved organic compounds and positive and negative ions. Subsequently, water in the deicing fluid is separated by distillation, possibly under vacuum, until the mixture of glycol/water has obtained the desired concentration.

However, at airports, where deicing fluid comprising thickener is used, problems arise in connection with the recovery of glycol. The thickener comprises a polymer, a polar organic compound, and long polymer chains thereof block the material in the ion exchange plant. The capacity of the ion exchange material is then strongly reduced with extensive operational breakdowns as a result. The capacity of the ion exchange material is also reduced by anionic tensides and petroleum products, e.g. hydraulic oil, aircraft fuel etc., which, in many cases, contaminate the glycol.

A process for recovery of glycol, among other things deicing fluid, is for instance disclosed in the Canadian Patent Application CA-A1-2116827. In this purification process fats, oils, and dirt are first separated from the used glycol in a sedimentation tank having a partition wall consisting of a metal mesh. The fluid is left to stand in the sedimentation tank until heavy solid particles have fallen down to the bottom of the tank and light organic compounds, such as fuel and hydraulic oils, float on the surface. The organic compounds are then removed from the surface by means of a pump. Purified glycol is removed from the sedimentation tank as an intermediate phase for further purification in a column packed with packing material of stainless steel, wherein water is evaporated by means of hot air before the glycol is further purified and concentrated by vacuum distillation. The vaporized water containing buffer, volatile organic compounds and other additives occurring in the deicing fluid must then be purified in a separate process.

THE INVENTION

The object of the invention is to remove the above referenced drawbacks with the method of the invention.

The object of the invention is also to achieve a device for purification of deicing fluid for recovery of glycol.

Due to the method and the device according to the invention, organic compounds, such as thickener, petroleum products and anionic tensides occurring in the deicing fluid, may be separated from the deicing fluid. In this way, damage on the material in the ion exchangers is avoided, and, according to the invention, allowing all kinds of deicing fluids to be purified and recovered with a higher degree of purification than has earlier been possible to achieve. A high degree of purification of the water separated during distillation is also achieved, said water not requiring any extra purification but can be discharged directly to the sewage system.

SHORT DESCRIPTION OF THE DRAWING

For further explanation of the invention, an example of an embodiment thereof will be described in more detail below with reference to the appended drawing showing a flow chart of a device according to the invention for the purification of deicing fluid for recovery of glycol.

DETAILED DESCRIPTION OF THE INVENTION

When arriving to the recycling device, the deicing fluid normally has a glycol content of 15–25 weight-% (monopropylene, monoethylene or diethylene) with an addition of thickener, normally a maximum of 1% of the total amount of glycol. In addition, additives of anionic and/or nonionic tensides, corrosion inhibitors and, in certain cases, colourings in a mixture with water, solid particles, salts etc. are included. Since the deicing fluid normally is buffered, it has a pH of about 6–8.

The purification process begins with flocculation of the deicing fluid in order to obtain a formation of larger aggregates of the colloids which are present in the liquid, especially the polymer chains of the thickener. The tendency of the particulate phase in colloidal dispersions to form aggregates is an important physical property which is utilized by many different separation processes, e.g. sedimentation and filtration. The formation of aggregates of colloids is denoted as coagulation or flocculation depending on how large forces are acting between the colloids in the aggregate.

Particles dispersed in a fluid collide due to relative motions (Brownian motions), and the stability of the dispersion (i.e. the stability against formation of aggregates) is determined by the interaction between the particles during these collisions. The forces of retraction and repulsion between the particles depend on the conditions in the fluid, e.g. salt concentration, pH etc.

Most particles achieve an electric charge on the surface when they come in contact with a polar medium. Ions having opposite charges in the fluid are attracted to the surface of the polar particle and ions having opposite charges repel. This process, together with the motions of the particles in the liquid, results in the formation of a diffuse electric double layer. In order to decrease the diffuse double layer of the particles and, thus, decrease the distance between the colloids, a flocculating agent is added which contains ions having a charge which is opposite to the charge of the colloid surface. Due to the flocculating agent, Van der Waals forces, which only are active at very short distances between the particles, may exist between the colloids in the solution such that larger aggregates, so called flocculate, may be formed. Subsequently, the flocculate can be separated from the solution in a subsequent separation process.

The macromolecules of the thickener included in the deicing fluid comprise polar polymer chains which have a negative surface charge in the deicing fluid. In order to increase the attraction forces between the repelling colloids, according to the invention, different flocculating agents have been tested, for example $CaCl_2$, alum and $Fe_2(SO_4)_3$, wherein the latter has been shown to be superior regarding kinetics, efficiency, yield, etc.

In order to achieve an efficient flocculation with $Fe_2(SO_4)$, it is essential that the amount of free $Fe^{3+}$ ions is sufficient. The concentration of $Fe^{3+}$ ions depends on the pH of the solution which also affects the formation of positive or negative hydroxyl complexes and deposition of $Fe(OH)_3$. The optimal amount of $Fe_2(SO_4)_3$ and the correct pH minimize the total content of dissolved iron in the purified liquid, which minimizes the load on the cation exchanger. An optimal pH range for flocculation of deicing fluid has proved to be 3.2<pH<4.8.

Referring to the FIGURE, the device for recovery according to the invention includes a collecting tank 1 for receiving deicing fluid, collected from an airport. Subsequently, $Fe_2(SO_4)_3$ is added to the deicing fluid in the collecting tank from a dosage tank 2 for $Fe_2(SO_4)_3$ through a conduit 3 by means of a dosage pump 4 until pH for the solution is within the range of 3.2<pH<4.8. For the measurement of the pH value in the deicing fluid, a not shown pH meter may be provided in the collecting container 1 or samples may be taken for an analysis. The concentration of $Fe_2(SO_4)_2$ solution in the deicing fluid should be at least 0.001 M.

As an example, it may mentioned that, in a deicing fluid having an addition of thickener which is about 1% of the total amount of glycol, an addition of about 1.0% by volume $Fe_2(SO_4)_3$ having a concentration of 0.1M is suitable. This results in a total concentration of $Fe^{3+}$ ions in the solution of about 100 ppm and a pH of about 3.2–4.8. In cases where the deicing fluid is strongly buffered, it may be required to add a larger amount of $Fe_2(SO_4)_3$ solution in order to achieve the desired pH; possibly some kind of acid may be added, for example HCl, in order to further decrease pH.

In order that the formation of flocculate in the deicing fluid shall be optimal, it is important that the $Fe_2(SO_4)_3$ solution is thoroughly mixed with the deicing fluid, and, for this purpose, the collecting tank 1 is provided with an agitator 5. The kinetics for the deicing fluid further requires that the flocculation is maintained for at least 2 hours in order that the yield shall be as large as possible. In certain cases, it may be necessary with a much longer time or flocculation, possibly up to 12 hours. In the collecting tank 1, heavier particles, such as sand and gravel from the apron, sink down to the bottom at the same time as the polymer chains of the thickener subsequently gather into larger aggregates, so called flocculate.

As an alternative to the collecting tank 1, an elongated narrow collecting vessel may be used, wherein the deicing fluid is supplied at one end of the vessel simultaneously with the flocculating agent. Then, the fluid is slowly transported through the length of the vessel such that the dwell time within the vessel is at least two hours before any deicing fluid is collected at the other end of the collecting vessel.

When the flocculation is finished, the deicing fluid is collected through a conduit 6 in order to be transported to a separator 7, for example an Alfa-Laval separator of the type used for example within the dairy industry for the separation of different phases of liquid food. The liquid is fed into the separator 7 through an inlet 8 at the bottom thereof. Since the flocculation process takes place batchwise, it may be suitable to provide several collecting tanks 1, as is shown on the drawing, to make a continuous flow of deicing fluid from the collecting tanks 1 to a separator 7 possible.

After the centrifugation in the separator 7, remaining heavier dust particles and the flocculated material may be collected as a heavy phase through an outlet conduit 9 at the bottom of the separator. Existing oils, for example hydraulic oil and diesel oil, and aircraft fuel are separated as a light phase through an outlet conduit 10 at the top of the separator and are thereafter collected in an exhaust tank 11. The deicing fluid, now being purified from petroleum products, flocculated material comprising the thickener and other larger particles >0.5 µm, is collected through an outlet conduit 12.

As the cation exchanger is damaged by $Fe^{3+}$ ions, the concentrations thereof should not exceed 10 ppm. For this purpose, a sand filter 13 is provided which, for example, comprises silica sand having a particle size of 0.8–1.2 mm and in which the concentration of $Fe^{3+}$ ions is decreased to <4 ppm. Flocculate remaining in the sand bed, which possibly may occur, is collected, and for this purpose it is important that the sand filter is provided directly after the separator. The sand filter may, if necessary, be cleaned by so called back flashing.

After the sand filter 13, the deicing fluid is collected through a conduit 14 and, if necessary, the device may be completed with a Mn-filter and/or a solids filter 15 having a mesh width of about 0.1–0.5 µm. Then, the purified deicing fluid is passed through an ion exchanger 16, normally comprising a humus filter (for the separation of organic compounds), a cation exchanger (for the separation of positive ions) and an anion exchanger (for the separation of negative ions). Finally, the deicing fluid is distilled in a not shown distillation column, wherein water is vaporized from the purified glycol until the mixture of glycol/water has obtained the desired concentration.

Due to the method and the device for the purification of deicing fluid according to the invention, the deicing fluid may pass through an ordinary ion exchanger comprising a humus filter, for the separation of organic material, and a cation and anion exchanger, for the separation of positive and negative ions, without the ion exchangers being damaged with long term breakdowns and economical drawbacks as a consequence thereof.

What is claimed is:

1. A method of purification of a deicing fluid comprising glycol and a polymer thickener, and optionally anionic tensides, and petroleum products for the recovery of glycol, the method comprsing:

adding $Fe_2(SO_4)_3$ to the deicing fluid as a flocculating agent;

maintaining, after the adding of the $Fe_2(SO_4)_3$, the pH of the deicing fluid within the range of pH 3.2–4.8;

mixing the deicing fluid and the $Fe_2(SO_4)_3$;

separating solid particles and flocculated material including said polymer thickener from the deicing fluid;

separating dissolved organic compounds and positive and negative ions from the deicing fluid via an ion exchanger; and separating water from the deicing fluid by means of distillation.

2. The method of claim 1, wherein the concentration of $Fe_2(SO_4)_3$ in the deicing fluid is at least 0.001 M.

3. The method of claim 1, wherein the adding step occurs at least two hours before the step of separating solid particles.

4. The method of claim 1, wherein the deicing fluid is separated in a separator, wherein flocculated material and the solid particles are collected as a heavy phase, light organic compounds are collected as a light phase and separated deicing fluid is collected as an intermediate phase.

5. The method as in claim 4, wherein the separated deicing fluid is passed through a sand filter in order to remove remaining solid particles and decrease the concentration of $Fe^{3+}$ ions in the separated deicing fluid.

6. The method as in claim 4, wherein the separated deicing fluid is passed through at least one of an Mn-filter and a solids filter having a mesh width of 0.1–0.5 $\mu$m.

* * * * *